US010792288B2

(12) United States Patent
Likitlersuang et al.

(10) Patent No.: US 10,792,288 B2
(45) Date of Patent: Oct. 6, 2020

(54) PRESERVATIVE FREE BRIMONIDINE AND TIMOLOL SOLUTIONS

(71) Applicant: Allergan, Inc., Irvine, CA (US)

(72) Inventors: Sukhon Likitlersuang, Irvine, CA (US); Ajay Parashar, Irvine, CA (US); Chetan P. Pujara, Irvine, CA (US); William F. Kelly, Rancho Santa Margarita, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 16/245,026

(22) Filed: Jan. 10, 2019

(65) Prior Publication Data

US 2019/0307759 A1 Oct. 10, 2019

Related U.S. Application Data

(63) Continuation of application No. 13/812,599, filed as application No. PCT/US2011/045656 on Jul. 28, 2011, now Pat. No. 10,213,431.

(60) Provisional application No. 61/368,681, filed on Jul. 29, 2010.

(51) Int. Cl.
*A61K 31/498* (2006.01)
*A61K 31/5377* (2006.01)
*A61K 9/00* (2006.01)
*A61K 9/08* (2006.01)
*A61K 47/02* (2006.01)
*A61K 47/12* (2006.01)

(52) U.S. Cl.
CPC ........ *A61K 31/5377* (2013.01); *A61K 9/0048* (2013.01); *A61K 9/08* (2013.01); *A61K 31/498* (2013.01); *A61K 47/02* (2013.01); *A61K 47/12* (2013.01)

(58) Field of Classification Search
CPC .... A61K 31/498; A61K 31/5377; A61K 9/08; A61K 9/00; A61K 47/02; A61K 47/12
See application file for complete search history.

(56) References Cited

U.S. PATENT DOCUMENTS

| | | | |
|---|---|---|---|
| 3,890,319 | A | 6/1975 | Danielewicz et al. |
| 4,195,085 | A | 3/1980 | Stone |
| 5,502,052 | A | 3/1996 | DeSantis |
| 2003/0199507 | A1 | 10/2003 | Chang |
| 2006/0198892 | A1 | 9/2006 | Ellis |

FOREIGN PATENT DOCUMENTS

| | | |
|---|---|---|
| EP | 0426390 | 8/1991 |
| EP | 2033649 | 11/2009 |
| WO | 2003088973 | 10/2003 |
| WO | 2008-024846 | 2/2008 |
| WO | 2011087790 | 7/2011 |

OTHER PUBLICATIONS

Allergan, Combigan Patient Information Leaflet, Allergan Pharmaceuticals (Pty) Ltd, 2006, 1-5.
Alphagan: PubChem, 2019, retrieved from https://pubchem.ncbi.nlm.nih.gov/compound/brimonidine_tartrate on May 13, 2019, pp. 1-26.
Bagnis, A., et al., Antiglaucoma drugs: The role of preservative-free formulations, Sadi J. Ophthalmol., 2011, 389-394, 25.
Baudouin, C., et al., Detrimental effect of preservatives in eyedrops: implications for the treatment of glaucoma, Acta Ophthalmol., 2008, 716-726, 86.
BNF, Brimonidine Tartrate, retrieved from https://bnf.nice.org.uk/drug/brimonidine-tartrate.html on May 13, 2019, pp. 1-6.
European Medicines Agency, EMEA Public Statement on Antimicrobial Preservatives in Opthalmic Preparations for Human USE, EMEA, 2009, 1, London, pp. 1.
European Patent Office (EPO), Communication of a notice of opposition, Examining Division, dated 2019, pp. 1-42.
Hopes, M., et al., Preservative-free Treatment in Glaucoma is a Sensible and Realistic Aim for the Future, Eur. Ophthalmic Rev., 2010, 23-28, 4.
Int'l Glaucoma Association, Alphagan Package Leaflet: Information for the User, Allergan Pharmaceuticals (Pty) Ltd, 2014, 1-6.
Kent, C., Preserving Without Preservatives, Rev. Ophthal., 2019, 1-3.
Moisseiev, E., et al., Intraocular pressure reduction using a fixed combination of timolol maleate 0.5% and brimonidine tartrate 0.2% administered three times daily, Clinical Ophthalmology, 2013, 1269-1273, 7.
Yee, R.W., The effect of drop vehicle on the efficacy and side effects of topical glaucoma therapy: a review, Curr. Opinion in Ophthalmol., 2007, 134-139, 18.
Baudouin, C., et al., Preservatives in eyedrops: The good, bad, and the ugly, Prog. Retinal & Eye Res., 2010, 312-334, 29.
European Patent Office (EPO), Communication of a notice of opposition, Examining Division, dated 2019, 1-17.
Abelson, Mark, The Secret World of Pharmacokinetics: Knowing something about this area of research can help make a better clinician, Rev. Ophthalmol., 2009, 10 pages.
Brimonidine Tartrate 0.2% / Timolol 0.5% Ophthalmic Solution NDA 21-398, 2012, 13 Pages.
Combigan Product Label, Allergan, Inc., 11 pages, 2008.
Heijl, Anders et al, Reduction of Intraocular Pressure and Glaucoma Progression: Results From the Early Manifest Glaucoma Trial, Arch Ophthalmol, 2002, 1268-1279, 120.
Jaenen, N. et al, Ocular Symptoms and Signs with Preserved and Preservative-Free Glaucoma Medications, European Journal of Ophthalmology, 2007, 341-349, 17(3).
Larsson, Lil-Inger, The Effect on Diurnal Intraocular Pressure of the Fixed Combination of Latanoprost 0.005% and Timolol 0.5% in Patients With Ocular Hypertension, Acta Ophthalmol. Scand., 2001, 125-128, 79.

(Continued)

*Primary Examiner* — Zohreh A Fay
(74) *Attorney, Agent, or Firm* — Lorenz Siddiqi

(57) ABSTRACT

The present invention is directed to preservative-free solutions of brimonidine and timolol for lowering intra-ocular pressure and treatment of glaucoma.

17 Claims, No Drawings

(56) References Cited

OTHER PUBLICATIONS

Lee, Anne et al, Fixed Combination of Topical Brimonidine 0.2% and Timolol 0.5% for Glaucoma and Uncontrolled Intraocular Pressure, Clinical Ophthalmology, 2008, 545-555, 2(3).

Leung, Eamon et al, Prevalence of Ocular Surface Disease in Glaucoma Patients, J Glaucoma, 2008, 350-355, 17.

Liang, Hong et al, Comparison of the Ocular Tolerability of a Latanoprost Cationic Emulsion Versus Conventional Formulations of Prostaglandins: An in Vivo Toxicity Assay, Molecular Vision, 2009, 1690-1699, 15.

Louati, Y. et al., Controversy: Is Benzalkonium Chloride Necessary in Anti-glaucoma Drops?, Journal of Current Glaucoma Practice, 2012, 104-107, 6 (3).

NDA 18-086/S-070 & NDA 18-086/S-072, Timoptic, Merck & Co., 1995.

Yuksel, Nurgen et al., The Short-Term Effect of Adding Brimonidine 0.2% to Timolol Treatment in Patients with Open-Angle Glaucoma, Ophthalmologica, 1999, 228-233, 213.

PRESERVATIVE FREE BRIMONIDINE AND TIMOLOL SOLUTIONS

CROSS REFERENCE TO RELATED APPLICATIONS

This application is a continuation of U.S. patent application Ser. No. 13/812,599, filed Jan. 28, 2013, which is a national phase application under 35 U.S.C. § 371 of PCT Patent Application No. PCT/US2011/045656, filed Jul. 28, 2011, which claims priority to U.S. Provisional Patent Application Ser. No. 61/368,681, filed on Jul. 29, 2010, each of which are incorporated herein by reference in their entireties and serve as the basis of a priority and/or benefit claim for the present application.

FIELD OF THE INVENTION

The present application is directed to preservative-free formulations of brimonidine and timolol.

BACKGROUND OF THE INVENTION

Brimonidine tartrate is a selective and potent alpha-2 adrenergic agonist. Brimonidine lowers intraocular pressure by reducing aqueous humor production and increasing uveoscleral outflow. Timolol maleate is a non-selective beta adrenergic receptor blocking agent. Currently marketed brimonidine and timolol combination ophthalmic solution with preservative is indicated for the reduction of elevated intraocular pressure (IOP) in patients with glaucoma or ocular hypertension who require adjunctive or replacement therapy due to inadequately controlled IOP.

Use of preservative containing eye drops has been implicated in the development or worsening of ocular surface disease. Management of open angle glaucoma and ocular hypertension require long term treatment with eye drops containing preservatives. Symptoms and signs of ocular surface disease such as ocular surface breakdown, irritation, burning, foreign body sensation, dryness, inadequate quantity of tears, etc. are prevalent in a large proportion of patients with open angle glaucoma and ocular hypertension.

Compared to eye drops preserved with benzalkonium chloride, preservative-free eye drops induce significantly fewer ocular symptoms and signs of irritation in patients, such as pain or discomfort, hyperemia, foreign body sensation, stinging or burning, and dry eye sensation.

Patients experiencing hypersensitivity reactions with benzalkonium chloride cannot use a commercial brimonidine and timolol products containing benzalkonium chloride which is preserved even with 0.005% w/v benzalkonium chloride. Benzalkonium chloride also may be absorbed by the soft contact lenses therefore patients wearing soft contact lenses are advised to remove lenses prior to administration and wait at least 15 minutes before reinserting them.

SUMMARY OF THE INVENTION

The present invention is directed to a brimonidine and timolol solutions without benzalkonium chloride or other preservatives which will be superior from a safety & tolerability standpoint while maintaining and/or improving its efficacy of IOP lowering and be available for use by patients hypersensitive to benzalkonium chloride and be convenient for patients wearing soft contact lenses.

Brimonidine and timolol ophthalmic solution without preservative is a clear, greenish-yellow, isotonic, sterile solution. The drug product contains brimonidine and timolol as the active ingredients. The inactive ingredients are tonicity and buffer agents, and purified water. Suitable buffers such as sodium phosphate dibasic heptahydrate and citric acid monohydrate and suitable tonicity agents such as sodium chloride may be included. The final solution would be an aqueous solution having a pH value within the range of about 6.5 to about 7.3, preferably 6.9 and osmolality in range of 260-220 mOsmol/kg.

The compositions of the present invention may be generally made according to the teachings of U.S. Pat. No. 7,323,463 which is hereby incorporated by reference in its entirety.

Certain embodiments of the present invention are described below:

1) A preservative free brimonidine and timolol composition for lowering intraocular pressure in a human patient comprising the following formulation: about 0.2% w/v brimonidine; about 0.5% w/v timolol; about 2.15% w/v sodium phosphate dibasic heptahydrate; water and at a pH of about 6.9.
2) A preservative free brimonidine and timolol composition for lowering intraocular pressure in a human patient comprising the following formulation: 0.2% w/v brimonidine; 0.5% w/v timolol; about 2.15% w/v sodium phosphate dibasic heptahydrate; hydrochloric acid, sodium hydroxide, and water and at a pH of about 6.9.
3) The preservative free composition of paragraphs 1-2 wherein the timolol is timolol maleate at 0.68% w/v and brimonidine is brimonidine tartrate.
4) A composition as described in Table 1.
5) The composition of any of paragraphs 1-4 wherein the composition is a solution and is useful for treating glaucoma.
6) The composition of any of paragraphs 1-4 wherein the composition is a solution and is contained in a unit dose kit form.
7) The composition of any of paragraphs 1-4 wherein the composition is applied at least once a day.
8) The composition of paragraph 2 wherein the composition is applied twice a day.
9) The composition of paragraphs 1 or 2 wherein the composition has greater bioavailability of brimonidine and timolol in the eye of the patient with fewer side-effects than brimonidine and timolol preserved with benzalkonium chloride.
10) The composition of paragraphs 1 and 2 wherein the composition is contained in a multi-dose vial which has anti-preservative properties such as metal-ions imbedded in its dispensing tip.
11) The composition of paragraph 12 wherein the metal ions are silver ions.

DETAILED DESCRIPTION OF THE INVENTION

A brimonidine and timolol ophthalmic formulation of the present invention without preservative is shown in Table-1.

TABLE 1

Example of brimonidine and timolol ophthalmic solution without preservative according to the present invention:

| Ingredients | Units | Grade | Amount |
|---|---|---|---|
| Brimonidine Tartarate | % w/v | N/A | 0.2 |
| Timolol Maleate | % w/v | USP/Ph Eur | 0.68 |

TABLE 1-continued

Example of brimonidine and timolol ophthalmic solution without preservative according to the present invention:

| Ingredients | Units | Grade | Amount |
|---|---|---|---|
| Sodium Phosphate Dibasic Heptahydrate | % w/v | USP | 2.15 |
| Sodium Phosphate Monobasic Monohydrate | % w/v | USP | 0.43 |
| Hydrochloric Acid | % w/v | USP/Ph Eur | pH 6.9 |
| Sodium Hydroxide | % w/v | USP/Ph Eur | pH 6.9 |
| Purified Water/Water for injection | Q.S. | USP/Ph Eur | QS |

The present invention is directed to formulations of brimonidine and timolol without benzalkonium chloride as a preservative. As a result of the removal of benzalkonium chloride, the present invention results in the same or greater bioavailability of the active ingredients bimatoprost and timolol in the eye without the unwanted side-effects associated with the preservative benzalkonium chloride which will improve efficacy of the product in lowering TOP per dosage unit, superior patient compliance and with fewer side-effects such as hyperemia. Other side effects which may be avoided include asthenia, blepharitis, corneal erosion, depression, epiphora, eye discharge, eye dryness, irritation, eye pain, eyelid edema, eyelid erythema, eyelid pruritus, foreign body sensation, headache, hypertension, oral dryness, somnolence, superficial pectate keratitis, and visual disturbance.

The invention claimed is:

1. A preservative free brimonidine and timolol composition for lowering intraocular pressure in a human patient comprising the following formulation: about 0.2% w/v brimonidine tartrate; about 0.68% w/v timolol maleate; about 2.15% w/v sodium phosphate dibasic heptahydrate; about 0.43% w/v sodium phosphate monobasic heptahydrate and water wherein the preservative free brimonidine and timolol composition dosed twice a day lowers intraocular pressure to a greater degree as compared to a second composition dosed twice a day comprising about 0.2% w/v brimonidine tartrate; about 0.68% w/v timolol maleate; about 0.005% benzalkonium chloride; about 2.15% w/v sodium phosphate dibasic heptahydrate; about 0.43% w/v sodium phosphate monobasic heptahydrate and water.

2. A preservative free brimonidine and timolol composition for lowering intraocular pressure in a human patient comprising the following formulation: 0.2% w/v brimonidine tartate; 0.68% w/v timolol maleate; about 2.15% w/v sodium phosphate dibasic heptahydrate; about 0.43% w/v sodium phosphate monobasic heptahydrate; hydrochloric acid, sodium hydroxide, and water and at a pH of about 6.9 wherein the preservative free brimonidine and timolol composition dosed twice a day results in fewer side effects of one selected from the group consisting of ocular pain, hyperemia, foreign body sensation, stinging or burning and dry eye sensation as compared to a second composition dosed twice a day comprising about 0.2% w/v brimonidine tartrate; about 0.68% w/v timolol maleate; about 0.005% benzalkonium chloride; about 2.15% w/v sodium phosphate dibasic heptahydrate; 0.43% w/v sodium phosphate monobasic heptahydrate, hydrochloric acid, sodium hydroxide and water and at a pH of about 6.9.

3. The preservative free composition of claim 1 wherein the timolol maleate is at 0.68% w/v.

4. A composition for use in the treatment of elevated intraocular pressure or glaucoma in a patient suffering therefrom comprising about 0.2% w/v brimonidine tartrate; about 0.68% w/v timolol maleate; about 2.15% w/v sodium phosphate dibasic heptahydrate; about 0.43% w/v sodium phosphate monobasic heptahydrate; hydrochloric acid, sodium hydroxide and water and at a pH of about 6.9 wherein the composition is preservative free.

5. The composition of claim 1 wherein the composition is a solution and is useful for treating glaucoma.

6. The composition of claim 1 wherein the composition is a solution and is contained in a unit dose kit form.

7. The composition of claim 4 wherein the composition is applied at least once a day.

8. The composition of claim 4 wherein the composition is applied at least twice a day.

9. The composition of claim 1 wherein the composition has greater bioavailability of brimonidine and timolol in the eye of the patient with fewer side-effects than brimonidine and timolol preserved with benzalkonium chloride.

10. A method of lowering intraocular pressure in a patient suffering from elevated intraocular pressure by administering the preservative free composition of claim 1.

11. The composition of claim 2 wherein the preservative free composition dosed twice a day results in less hyperemia in the patient as compared to the composition preserved with brimonidine tartrate.

12. The composition of claim 2 wherein the preserved composition dosed twice a day results in less burning and stinging in the patient as compared to the composition preserved with brimonidine tartrate.

13. The composition of claim 2 wherein the preserved composition dosed twice a day results in less dry eye in the patient as compared to the composition preserved with brimonidine tartrate.

14. The composition of claim 4 wherein the composition is a solution.

15. The composition of claim 4 wherein the preserved composition has better efficacy in a patient as compared to the same composition preserved with 0.005% w/v benzalkonium chloride when both compositions are applied twice a day.

16. The composition of claim 15 wherein the preserved composition lowers intraocular pressure to a greater degree as compared to the same composition preserved with 0.005% w/v benzalkonium chloride when both compositions are applied twice a day.

17. The composition of claim 15 wherein the preserved composition results in fewer side effects as compared to the same composition preserved with 0.005% w/v benzalkonium chloride.

* * * * *

UNITED STATES PATENT AND TRADEMARK OFFICE
CERTIFICATE OF CORRECTION

| | | |
|---|---|---|
| PATENT NO. | : 10,792,288 B2 | Page 1 of 1 |
| APPLICATION NO. | : 16/245026 | |
| DATED | : October 6, 2020 | |
| INVENTOR(S) | : Sukhon Likitlersuang et al. | |

It is certified that error appears in the above-identified patent and that said Letters Patent is hereby corrected as shown below:

On the Title Page

Item (56), in Column 2, under "Other Publications", Line 14, delete "Opthalmic" and insert -- Ophthalmic --, therefor.

In the Specification

In Column 2, Line 64, delete "Tartarate" and insert -- Tartrate --, therefor.

In Column 3, Line 22, delete "TOP" and insert -- IOP --, therefor.

In Column 3, Line 26, before "irritation," insert -- eye --.

In Column 3, Line 29, delete "pectate" and insert -- punctate --, therefor.

In the Claims

In Column 3, Line 49, in Claim 2, delete "tartate;" and insert -- tartrate; --, therefor.

Signed and Sealed this
Twenty-ninth Day of December, 2020

Andrei Iancu
*Director of the United States Patent and Trademark Office*